United States Patent
Yao

(10) Patent No.: US 6,514,253 B1
(45) Date of Patent: Feb. 4, 2003

(54) APPARATUS FOR LOCATING INTERLOCKING INTRAMEDULLARY NAILS

(76) Inventor: Meei-Huei Yao, 62, Yung-Luh Rd., Ho-Mei Township, Chang-Hua County (TW)

( * ) Notice: Subject to any disclaimer, the term of this patent is extended or adjusted under 35 U.S.C. 154(b) by 255 days.

(21) Appl. No.: 09/717,027

(22) Filed: Nov. 22, 2000

(51) Int. Cl.[7] ............................................... A61B 17/56
(52) U.S. Cl. ............................ 606/53; 606/54; 606/95; 606/96; 602/5; 602/12; 602/21; 602/26; 602/27; 128/892
(58) Field of Search .............................. 606/76, 78, 80, 606/87, 88, 92, 95–100, 212, 216–221, 53, 54; 623/16.11, 20.14, 20.32, 20.35, 27; 602/5, 6, 12, 16, 19–31; 128/892

(56) References Cited

U.S. PATENT DOCUMENTS

| | | | | |
|---|---|---|---|---|
| 4,135,505 A | * | 1/1979 | Day ............................ | 128/92 |
| 4,667,664 A | * | 5/1987 | Taylr et al. .................... | 128/92 |
| 5,275,599 A | * | 1/1994 | Zbikowski et al. ........... | 606/54 |
| 5,474,561 A | | 12/1995 | Yao .............................. | 606/98 |
| 5,643,258 A | * | 7/1997 | Robioneck et al. ........... | 606/54 |
| 5,690,633 A | * | 11/1997 | Taylor et al. .................. | 606/73 |
| 6,235,029 B1 | * | 5/2001 | Faccioli et al. ................ | 606/54 |

* cited by examiner

Primary Examiner—Linda C. M. Dvorak
Assistant Examiner—A Farah
(74) Attorney, Agent, or Firm—Bacon & Thomas, PLLC

(57) ABSTRACT

An apparatus for locating interlocking intramedullary nails comprises a slide device which is disposed at the near end of the nails and is capable of adjustment in various directions. The slide device is provided with a locking structure, a locating rod, or drilling guide sleeve. The relative positions of the near end and the far end threaded holes of the interlocking intramedullary nails of various hole intervals and specifications are adjusted by the slide device in accordance with the body size of a patient under treatment. The drilling position of the drilling guide sleeve can be attained with precision and speed.

1 Claim, 10 Drawing Sheets

APPARATUS FOR LOCATING INTERLOCKING INTRAMEDULLARY NAILS

FIELD OF THE INVENTION

The present invention relates generally to an apparatus for use in an orthopedic surgery, and more particularly to an apparatus for locating the interlocking intramedullary nails.

BACKGROUND OF THE INVENTION

The U.S. Pat. No. 5,474,561 of the same applicant has disclosed an all positional and universal guiding device for interlocking intramedullary nail. Under such a prior art, the applicant devotes himself and creates a further development and precision apparatus for locating interlocking intramedullary nails.

The interlocking intramedullary nails are often used in treatment of deformities, diseases, and injuries of bones, such as humerus, femur, tibia, etc. The interlocking intramedullary nails are used in conjunction with the fixation nails for the rehabilitation of the deformed bone. Such restorative operation is often complicated by the fact that there are a variety of interlocking intramedullary nails, which are different in specification and are made by various manufacturers.

It is technically difficult to implant an interlocking intramedullary nail with precision. In order to minimize the technical difficulty that is involved in the implanting of the interlocking intramedullary nail, the X-ray machine is often used to help the surgeon to align the nail with the threaded hole. It is conceivable that the constant exposure to the X-rays is hazardous to the health of the surgeon.

SUMMARY OF THE INVENTION

The primary objective of the present invention is to provide an adjustable apparatus enabling the interlocking intramedullary nails of various specifications to be aligned with the near end and the far end threaded holes without the use of the X-ray machine.

The features and the advantages of the present invention will be more readily understood upon a thoughtful deliberation of the following detailed description of the present invention with reference to the accompanying drawings.

DETAILED DESCRIPTION OF THE PREFERRED EMBODIMENT

Figure 1:
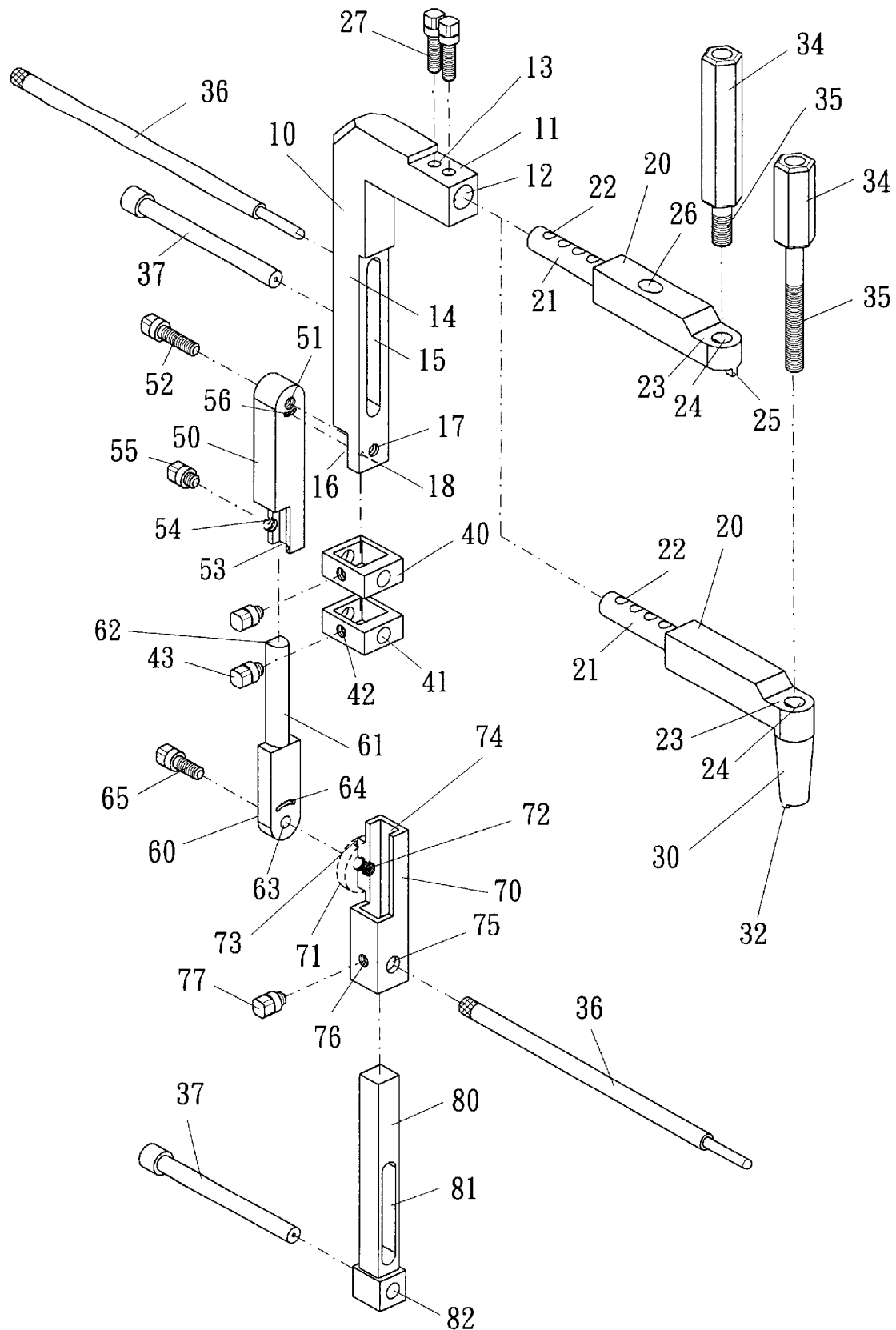
FIG. 1 shows an exploded view of the present invention.
Figure 2:
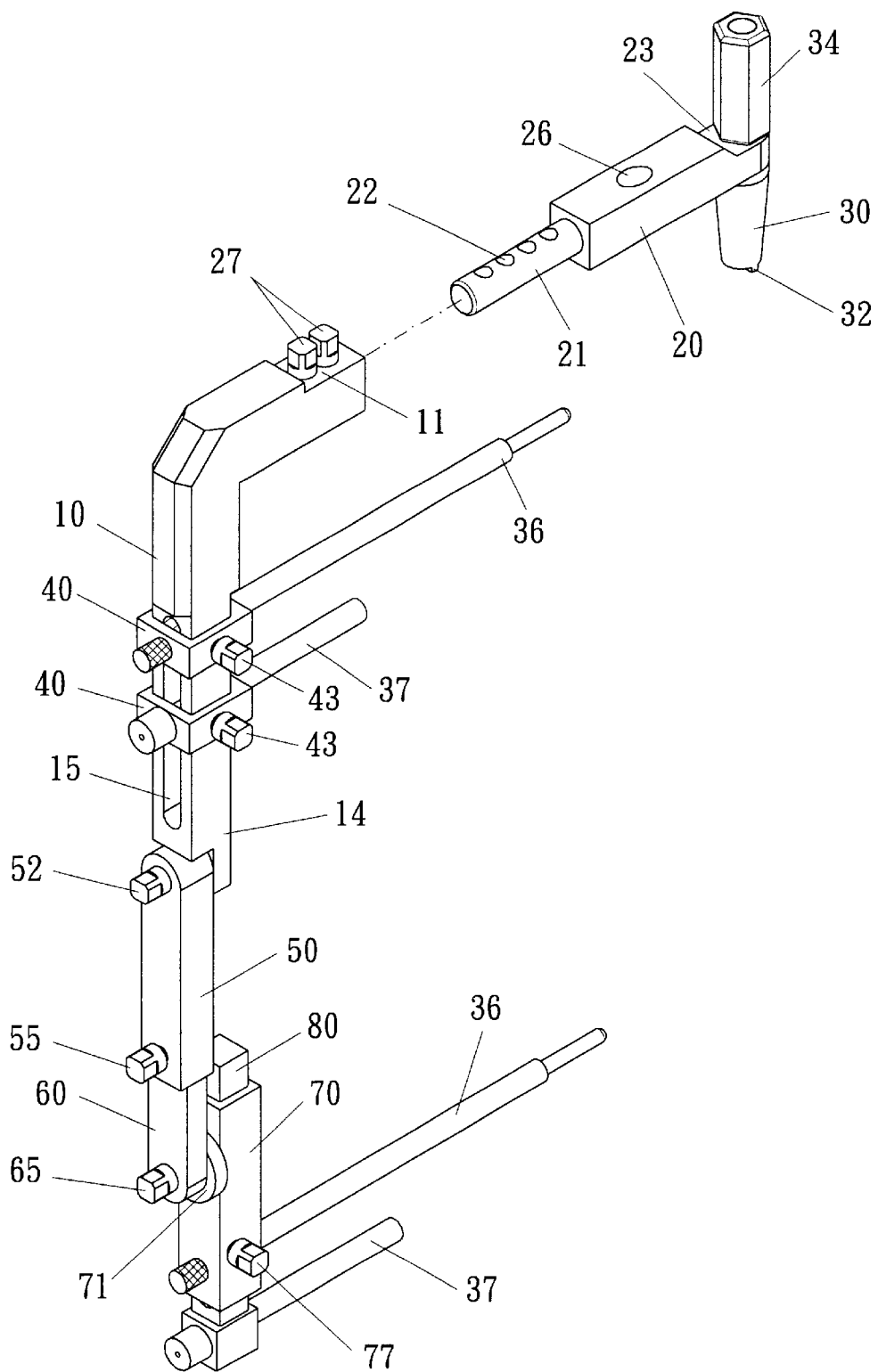
FIG. 2 shows a perspective view of the present invention in combination.

As shown in FIGS. 1 and 2, the present invention comprises a curved main body 10 and a vertical seat 11, which is perpendicular to the bone nail and is provided with and inner recessed hole 12 and a plurality of fastening holes 13. The main body 10 is provided with a parallel seat 14 which is parallel to the bone nail and is provided with a long slide slot 15 and a swaying seat 16 which is in turn provided with a locking hole 17. The locking hole 17 is provided at the outer end thereof with a protruded pillar 18. The inner recessed hole 12 of the vertical seat 11 of the main body 10 is provided with an extension seat 20 which is provided with an expandable rod 21 having a plurality of fitting holes 22 corresponding to the locking hole 13. The extension seat 20 is provided at other end thereof with a carrying seat 23 which is provided in the midsegment thereof with a through hole 24 which is provided at the bottom end thereof with a locating block 25 projecting therefrom. The extension seat 20 is further provided with a near end inclined hole 26 as desired. The locking hole 13 end of the main body 10 is provided with two threaded rods 27 to cooperate with the fitting hole 22. In light of various bone nail designs, the carrying seat 23 is provided at the bottom end thereof with a rotary connection block 30 which is in turn provided at the bottom end with an orientation locating block 32 for connecting the threaded rod 35 end of a nail connection rod 34. The parallel seat 14 is provided with two slide blocks 40 fastened thereto. The slide block 40 is provided with two retaining holes 41 in cooperation with the slide slot 15. The slide block 40 is provided in one side with a fixation thread 42 to cooperate with a threaded rod 43. The swaying seat 16 is provided with an adjustment swing arm 50 which is provided with an axial hole 51 to cooperate with the locking hole 17 so as to set up a threaded rod 52. The adjustment swing arm 50 is provided with a slide hole 53 and a locking hole 54 to cooperate a threaded rod 55. The protruded pillar 18 of the main body 10 is provided with an arcuate restriction slot 56. The adjustment swing arm 50 is provided at the bottom end thereof with an adjustment block 60 extending therefrom and having a locating slide shaft 61 to cooperate the slide hole 53 of the adjustment swing arm 50. The locating slide shaft 61 is provided at one end with a retaining face 62. The adjustment block 60 is provided at the front end with an axial hole 63 which is provided at the outer end with a recessed restriction slot 64. The axial hole 63 of the adjustment block 60 is connected with the locking hole 72 of the rotary seat 71 of a slide seat 70 by a threaded rod 65. The locking hole 72 is provided at the outer end with a protruded pillar 73 to cooperate with the restriction slot 64. The slide seat 70 is provided with a slide through hole 74 and a fitting hole 75. A threaded rod 77 is provided to fasten the locking hole 76 of the slide hole 74 in which an adjustment rod 80 is received. An opening hole 81 is corresponding to the fitting hole 75 of the slide seat 70. The adjustment rod 80 is provided at the front end with a fitting hole 82. Finally, the near end inclined hole 26, the retaining hole 41, the fitting holes 75, 82 are provided with a guide rod 36 or drilling guide sleeve 37.

Figure 3:
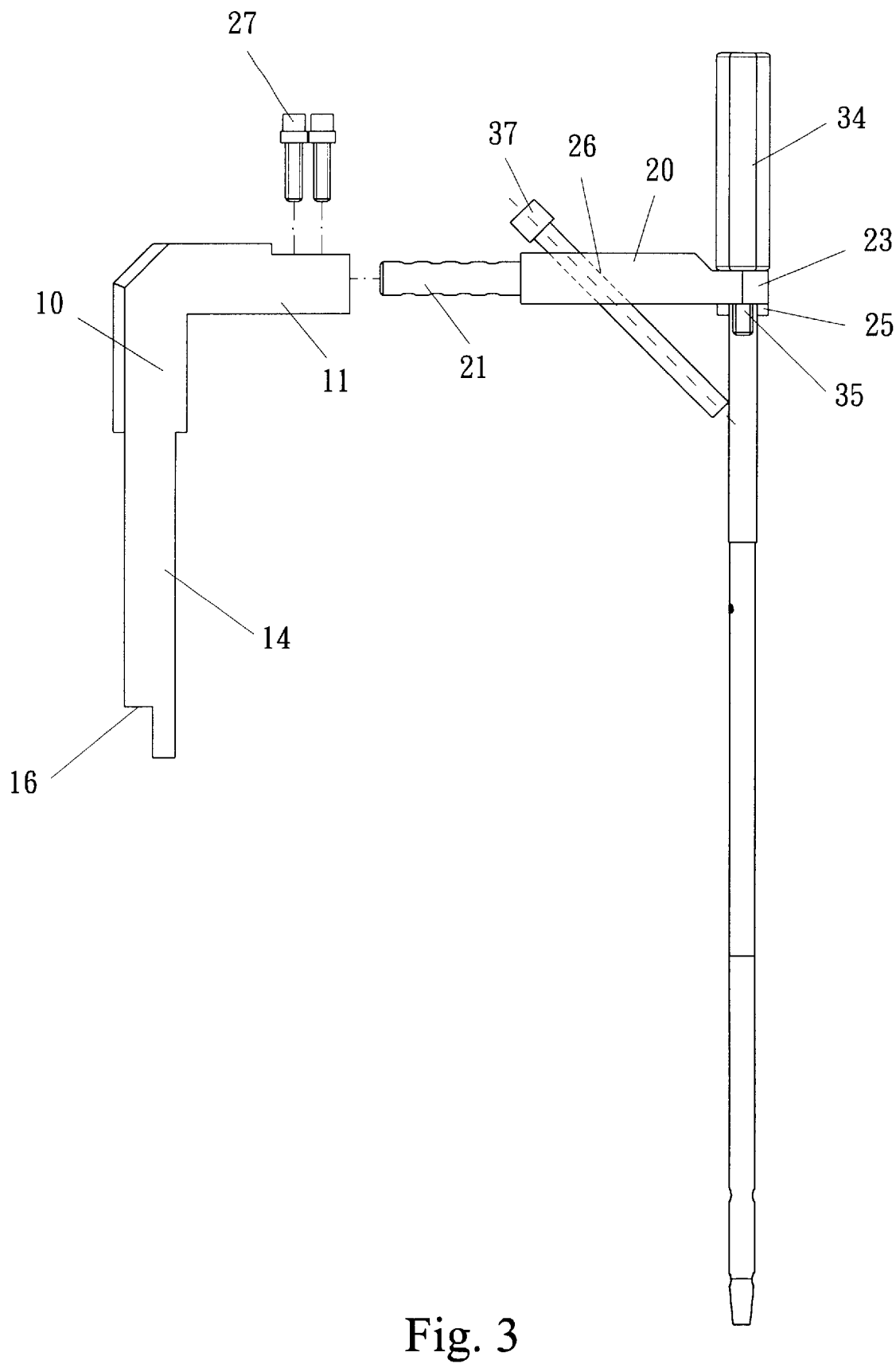
FIG. 3 shows a schematic view of the inclined near end threaded hole of the present invention.
Figure 4:
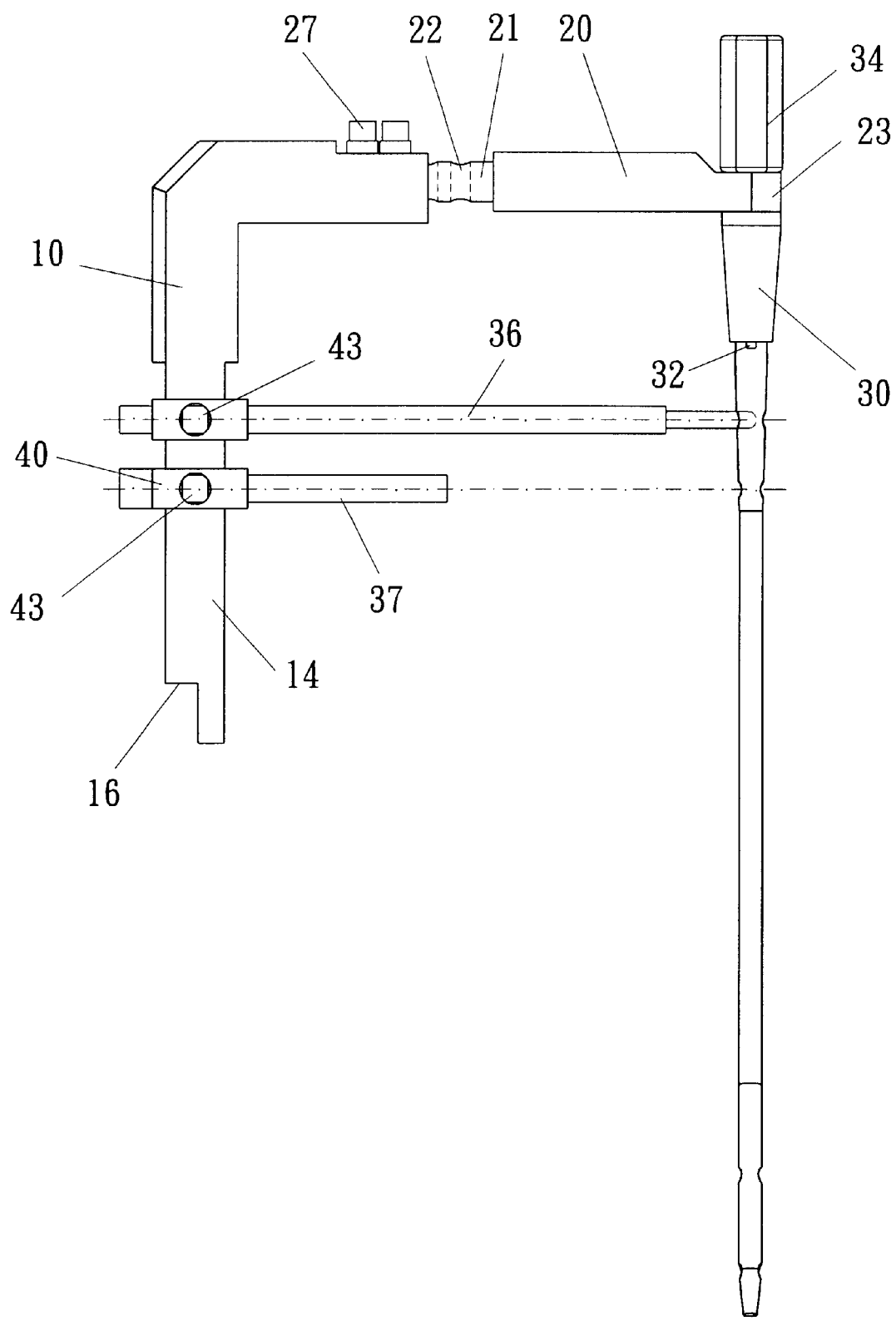
FIG. 4 shows a schematic view of another near end threaded hole of the present invention.
Figure 5:
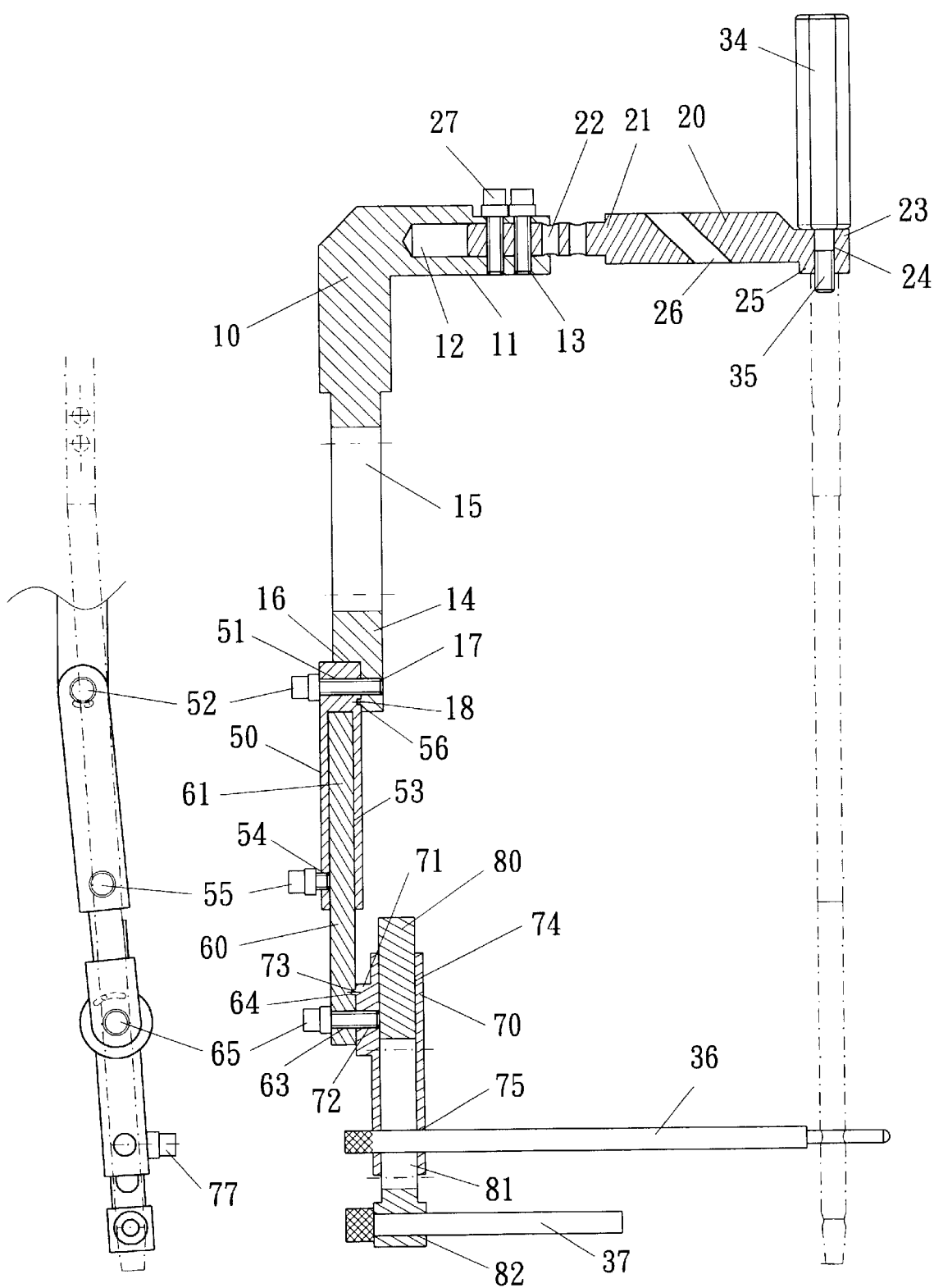
FIG. 5 shows a schematic view of the far end threaded hole of the present invention.

As shown in FIGS. 3–5, in conjunction with FIGS. 6–10, the component parts of the present invention can be easily separated or combined. They can be stored separately in an orderly manner. They can be stored separately in an orderly manner. They can be put together as required in cooperation with the interlocking intramedullary nails of various specifications.

Figure 8:
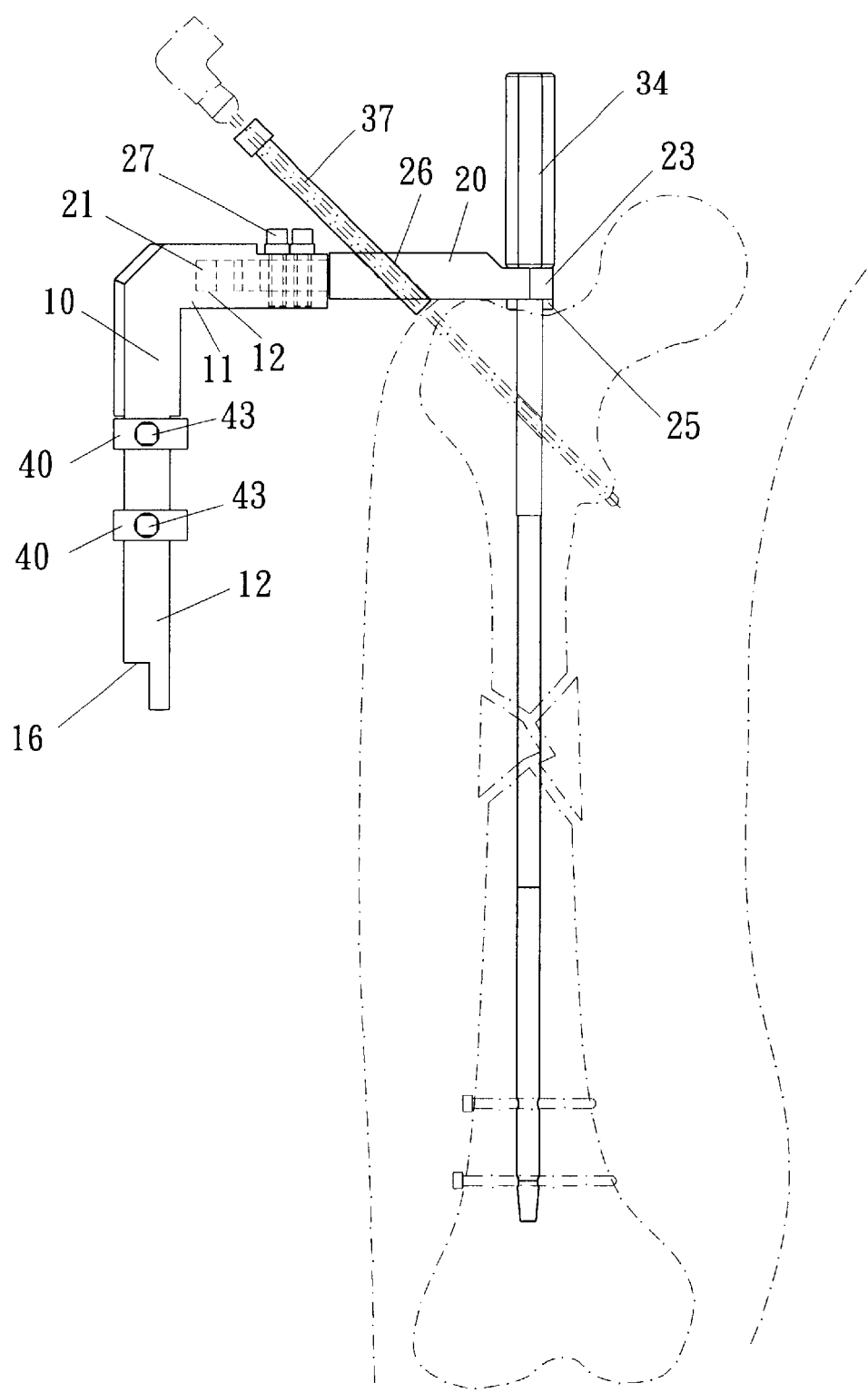
FIG. 8 shows a schematic view of the embodiment of the inclined near end threaded hole of the present invention.

As shown in FIG. 3, in light of the near end threaded hole of the interlocking intramedullary nail being of an inclined construction, only the extension seat 20 is called for such that the locating block 25 of the extension seat 20 is fitted with the interlocking intramedullary nail of an appropriate specification, and that it is fastened with the threaded rod 35 of the nail connection rod 34. The near end inclined hole 26 is provided with the drilling guide sleeve 37 for drilling the near end threaded hole, as shown in FIG. 8. The expandable rod 21 of the extension seat 20 can be cooperated with the body size of a patient such that it can be fixed in the inner recessed hole 12 by two threaded rods 27.

Figure 6:
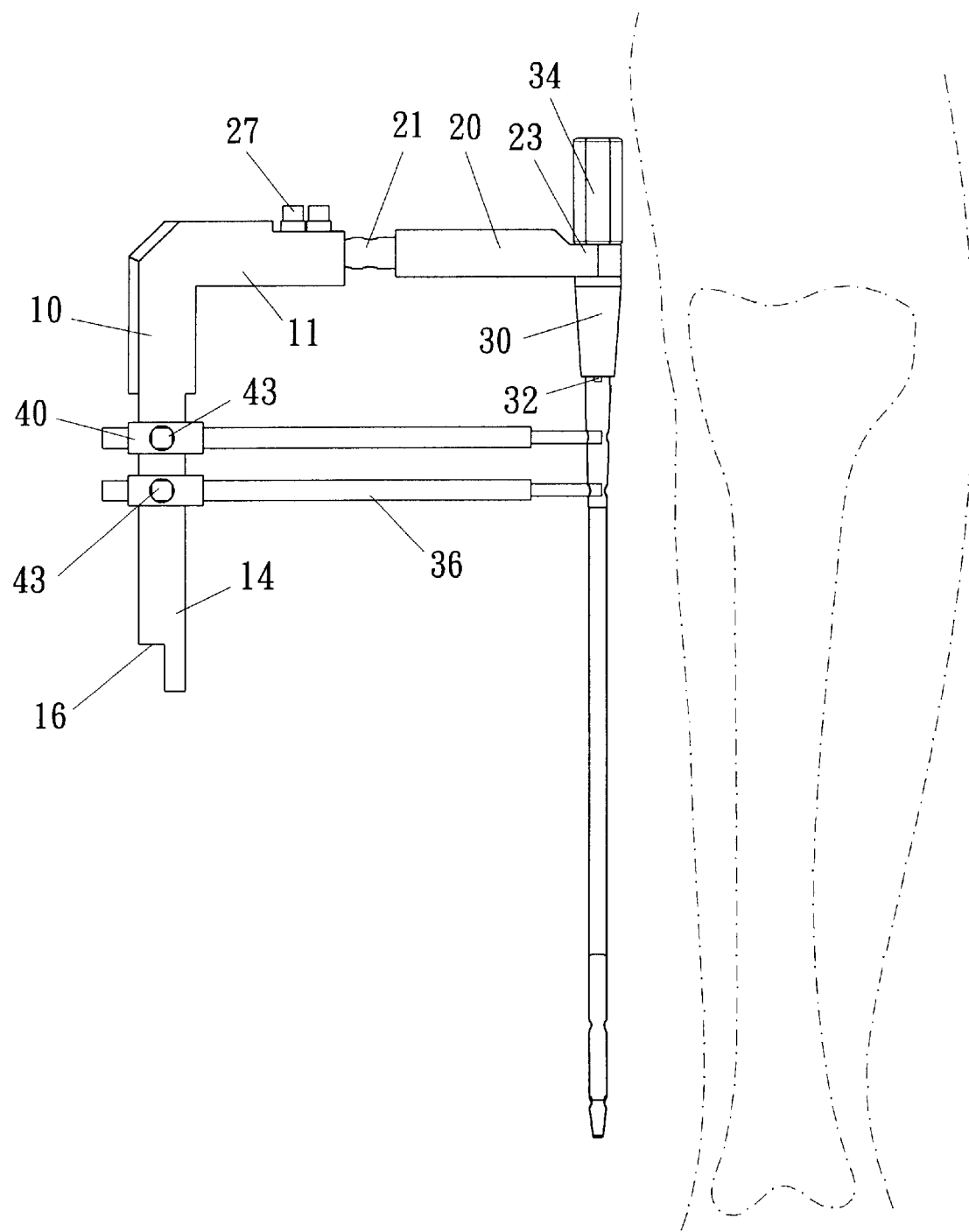
FIG. 6 shows a schematic view of a locating embodiment of another near end threaded hole of the present invention.
Figure 7:
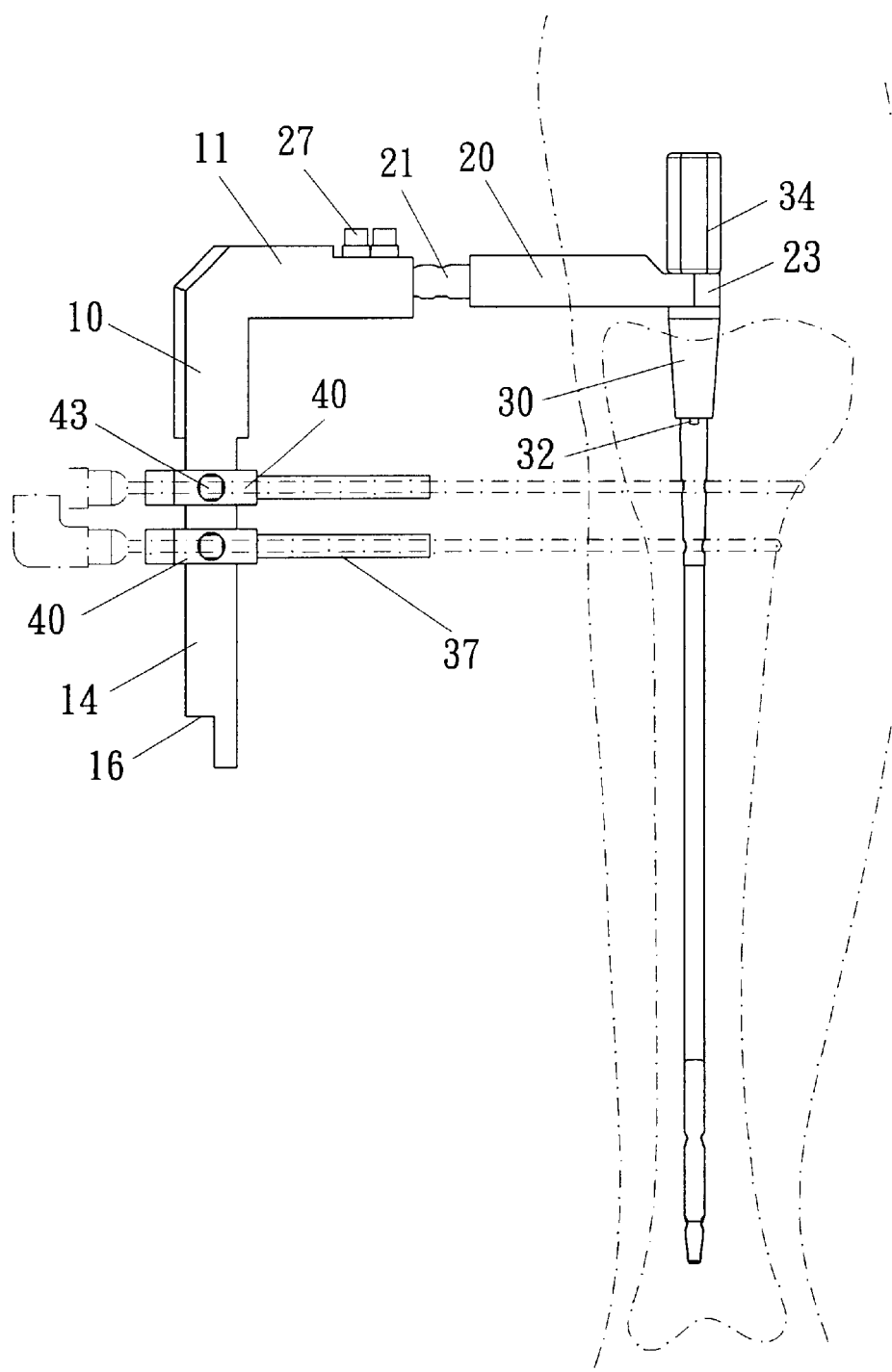
FIG. 7 shows a schematic view of a drilling embodiment of another near end threaded hole of the present invention.

As shown in FIG. 4, in light of the near end threaded hole of the interlocking intramedullary nail being perpendicular to the interlocking intramedullary nail end, the slide block 40 is fastened with the parallel seat 14 of the main body 10 after being fastened onto humerus, femur, or tibia. The interlocking intramedullary nails of various specifications are thus fastened by means of two guide rods 36 and the threaded rod 43, as shown in FIG. 6. The near end threaded holes of various intervals of interlocking intramedullary nails of various brands are thus located. Upon completion of the implanting of the nails onto humerus, femur, or tibia, the drilling guide sleeve 37 is connected to facilitate the work of drilling the near end threaded hole, as shown in FIG. 7.

Figure 9:
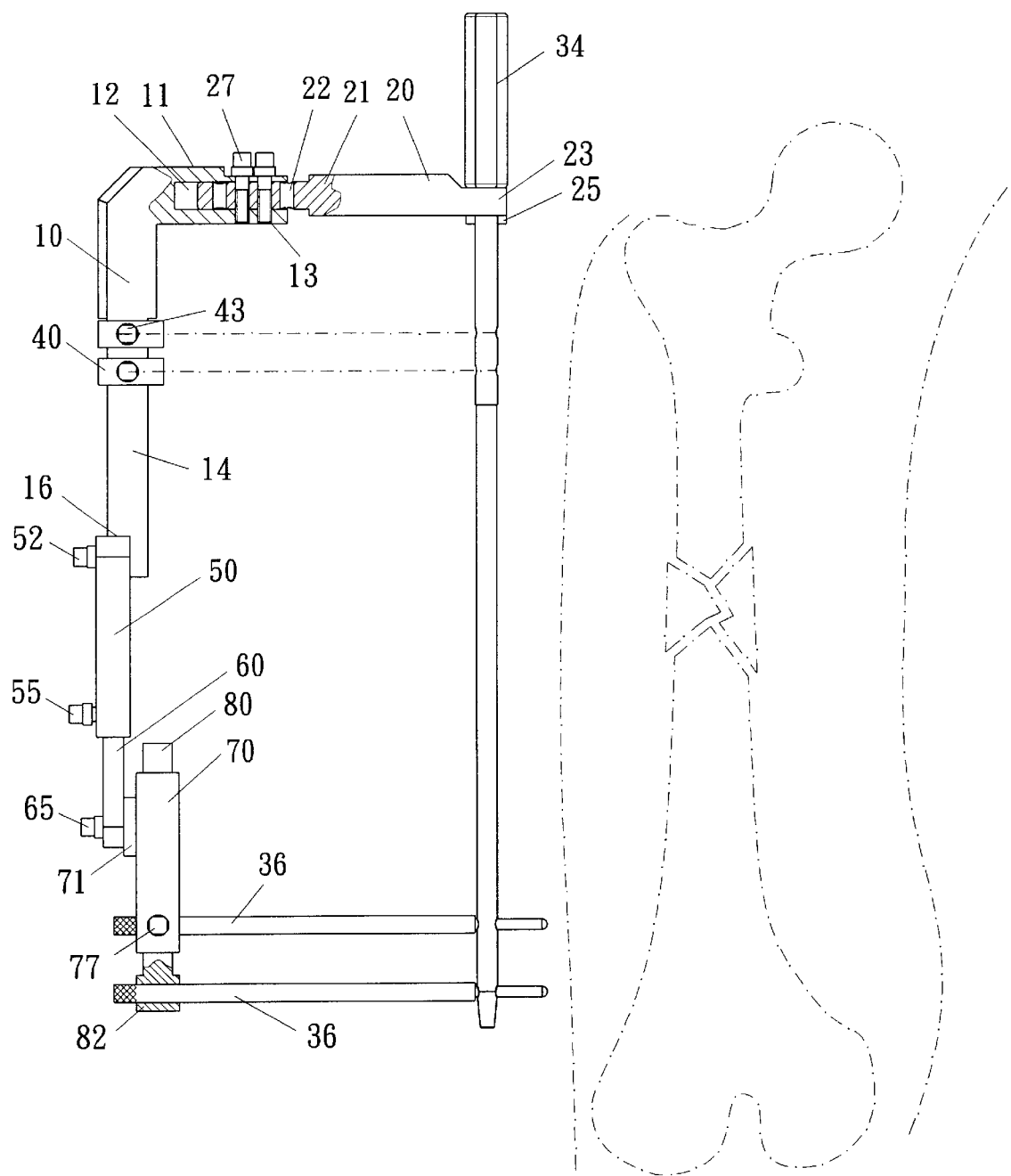
FIG. 9 shows a schematic view of a locating embodiment of the far end threaded hole of the present invention.
Figure 10:
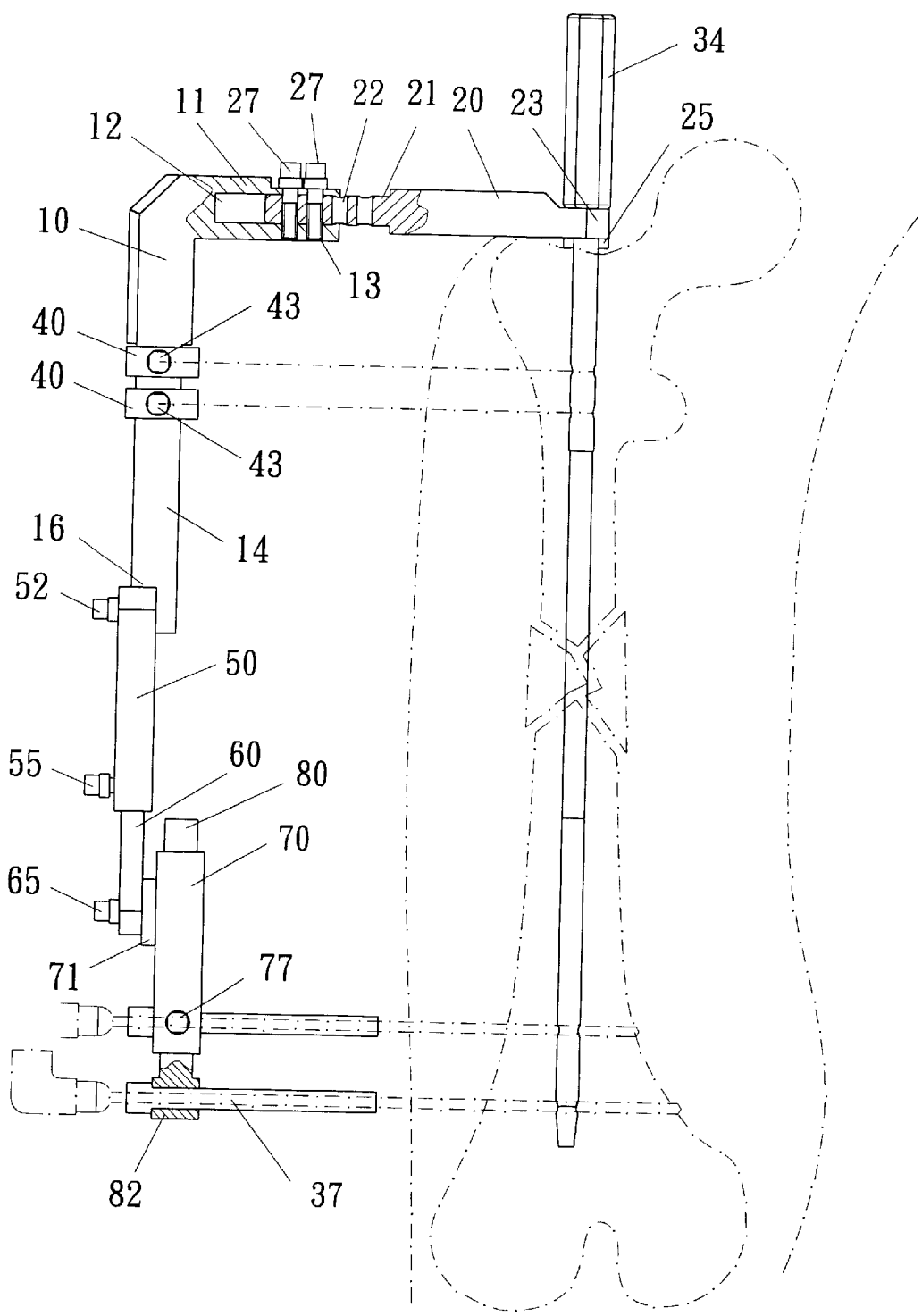
FIG. 10 shows a schematic view of a drilling embodiment of the far end threaded hole of the present invention.

As shown in FIG. 5, the far end threaded hole is located by the present invention. Upon completion of the fastening of the interlocking intramedullary nail, the adjustment swing arm 50 of an appropriate length is selected and then fastened by the threaded rod 55. The far end threaded hole member is formed of the adjustment block 60, the slide seat 70, and the adjustment rod 70. The far end threaded holes of the interlocking intramedullary nails are connected by two guide rods 36 in conjunction with the fitting holes 75 and 82. As the threaded rods 65 and 52 are unfastened, the protruded pillars 18 and 73 are located in the restriction slot 56, 64 respectively. The present invention is capable of cooperating with the curvature of the interlocking intramedullary nails. Upon completion of the fastening of the threaded rods 77, 65, 55, and 52, the parallel locating of the far end threaded holes is thus attained, as shown in FIG. 9. After the implantation of the interlocking intramedullary nail into femur, tibia, or humerus, the drilling guide sleeve 37 is fastened to facilitate the work of drilling the far end threaded hole, as shown in FIG. 10. In light of the interlocking intramedullary nails being various in length, it is necessary to unfasten the threaded rod 55 so as to adjust the relative positions of the locating slide shaft 61 and the slide hole 53 of the adjustment swing arm 50. For the purpose of locating the far end threaded holes of various brands, the threaded rod 77 is first unfastened so as-to adjust the two guide rods 36 in relation to the hole interval of various far end threaded holes of the interlocking intramedullary nails. The locating of the far end threaded holes of various brands can be also attained by adjusting the sliding distance of the adjustment rod 80 in the slide hole 74 of the slide seat 70. Finally, the threaded rod 77 is fastened to conclude the adjusting of the hole interval of the far end threaded holes of various brands.

Depending on the body size of a patient, the adjustment of the near end and the far end threaded holes of the interlocking intramedullary nails of various specifications is attained by changing the adjustment swing arm 50 and the adjustment block 60. The locating blocks 25 of various specifications can be adjusted by means of the expandable rod 21 of the extension seat 20. According to the bone size of the patient, the locating of the threaded holes, the drilling of the threaded holes, and the fastening of the threaded holes can be done by adjusting the distance between the deformed bone and the horizontal seat 14 of the main body 10, without the help of the X-ray machine.

What is claimed is:

1. An apparatus for locating interlocking intramedullary nails, said apparatus comprising a curved main body which is provided in a vertical seat thereof with a recessed hole and two locking holes, said main body further provided in a parallel seat thereof with a slide slot and a swaying seat having in the center a fastening hole which is provided with a protruded pillar, said recessed hole being provided with an extension seat which is provided at one end with an expandable rod having a fitting hole corresponding to said locking hole, said extension seat being provided at other end thereof with a carrying seat having in the midsegment thereof a through hole which is provided at the bottom end with a locating block, said extension seat further provided with a near end inclined hole, said locking hole of said main body provided with a threaded rod to cooperate with said fitting hole, said carrying seat provided at the bottom end thereof with a rotary connection block which is provided at the bottom end with an orientation locating block and a nail connection rod, said parallel seat provided with two slide blocks which are provided with two retaining holes and are provided in one side with a fixation thread and a threaded rod, said swaying seat being provided with an adjustment swing arm having an axial hole in cooperation with said fastening hole, said adjustment swing arm provided with a slide hole, a fastening hole, a threaded rod, and an arcuate restriction slot corresponding to said protruded pillar, said adjustment swing arm provided in the bottom end with an adjustment block having at one end a locating slide shaft in cooperation with said slide hole of said adjustment swing arm, said locating slide shaft provided at one end with a retaining face, said adjustment block provided at a front end with an axial hole which is provided at an outer end with a recessed restriction slot, said adjustment block being provided at said axial hole end with a threaded rod which is engaged with a fastening hole of a rotary seat of a slide seat, said fastening hole being provided at the outer end with a protruded pillar in cooperation with said restriction slot, said slide seat further provided with a slide hole and a fitting hole and in one side thereof with a threaded rod, said slide hole of said slide seat being provided with an adjustment rod and an opening hole corresponding to said fitting hole of said slide seat, said adjustment rod provided at the front end with a fitting hole whereby said near end inclined hole, said retaining hole, and said fitting hole are provided with a guide rod or drilling guide sleeve fastened therewith in cooperation with the interlocking intramedullary nails of selected specifications and having near, end threaded holes and far end threaded holes which are separated at selected intervals.

* * * * *